(12) United States Patent
Rehberger et al.

(10) Patent No.: US 6,887,489 B2
(45) Date of Patent: May 3, 2005

(54) PROPIONIBACTERIUM P-63 FOR USE IN DIRECT FED MICROBIALS FOR ANIMAL FEEDS

(75) Inventors: Thomas Rehberger, Milwaukee, WI (US); Terry D. Parrott, Waukesha, WI (US); Fred C. Owens, West Des Moines, IA (US); Charles A. Hibberd, Scottsbluff, NE (US)

(73) Assignee: The Board of Regents for Oklahoma State University, Stillwater, OK (US)

(*) Notice: Subject to any disclaimer, the term of this patent is extended or adjusted under 35 U.S.C. 154(b) by 0 days.

(21) Appl. No.: 10/209,735

(22) Filed: Aug. 1, 2002

(65) Prior Publication Data

US 2003/0007953 A1 Jan. 9, 2003

Related U.S. Application Data

(62) Division of application No. 09/292,720, filed on Apr. 15, 1999, now Pat. No. 6,455,063.
(60) Provisional application No. 60/082,067, filed on Apr. 17, 1998.

(51) Int. Cl.$^7$ ................................................ A23K 1/18
(52) U.S. Cl. ..................... 424/438; 424/93.1; 424/93.3; 424/93.4; 424/442; 426/2; 426/53; 426/61
(58) Field of Search ................................ 424/438, 442, 424/93.1, 93.3, 93.4–93.45; 426/61, 635, 636, 807, 2, 53

(56) References Cited

U.S. PATENT DOCUMENTS

| | | | |
|---|---|---|---|
| 4,980,164 A | 12/1990 | Manfredi et al. | 424/93 |
| 4,981,705 A | 1/1991 | Tomes | 426/53 |
| 5,096,718 A | 3/1992 | Ayres et al. | 426/9 |
| 5,139,777 A | 8/1992 | Ott et al. | 424/93 A |
| 5,256,425 A | 10/1993 | Herman et al. | 424/93 J |
| 5,260,061 A | 11/1993 | Ayres et al. | 424/115 |
| 5,529,793 A | 6/1996 | Garner et al. | 426/61 |
| 5,534,271 A | 7/1996 | Ware et al. | 426/2 |
| 5,945,333 A | 8/1999 | Rehberger | 435/268 |
| 6,120,810 A | 9/2000 | Rehberger et al. | 426/61 |
| 6,221,650 B1 | 4/2001 | Rehberger | 435/252.4 |
| 6,455,063 B1 * | 9/2002 | Rehberger et al. | 424/438 |

OTHER PUBLICATIONS

Database Dissertation Abstracts Online, Swinney–Floyd, Dara Lynn: "The Impact of Inoculation with Propionibacterium on Ruminal Acidosis in Beef Cattle (*Lactobacillus*)", retrieved from Dialog Database accession no. 01647688, XP002111092, and cross–referenced to Dissertation Abstracts International, vol. 59/05–B, 1997, p. 1928, US, Nov. 1998.

ProQuest Digital Dissertations—Full Citation and Abstract, Swinney–Floyd, Dara Lynn: "The Impact of Inoculation with Propionibacterium on Ruminal Acidosis in Beef Cattle (*Lactobacillus*)", retrieved from UMI online database, Oct. 12, 1999.

* cited by examiner

Primary Examiner—Neil S. Levy
(74) Attorney, Agent, or Firm—Fellers, Snider Blankenship, Bailey & Tippens, P.C.

(57) ABSTRACT

A ruminant direct fed microbial composition of matter comprising an acidosis inhibiting effective amount of *Propionibacterium* P-63 is provided. Also disclosed is a process for reducing acidosis in ruminants or scours in swine by administration of the bacterium to the ruminant or swine. The microbial composition may be administered by itself, or combined with animal feed and/or lactic acid producing cultures.

10 Claims, No Drawings

PROPIONIBACTERIUM P-63 FOR USE IN DIRECT FED MICROBIALS FOR ANIMAL FEEDS

This application is a divisional of application Ser. No. 09/292,720 filed on Apr. 15, 1999 now U.S. Pat. No. 6,455,063.

This application claims the benefit of Provisional Application No. 60/082,067 filed Apr. 17, 1998.

BACKGROUND OF THE INVENTION

1. Field of the Invention

The present invention relates generally to a process for improving the utilization of feedstuffs by ruminants, especially during the transition from a roughage diet to a feedlot diet, and more particularly to a process for administering to a ruminant a feed additive composition which includes *Propionibacteria jensenii* strain P-63, preferably in combination with a lactic acid producing bacteria for improving the production from, and feed conversion efficiency of, a high grain or concentrate feedlot diet. The composition also may be used to reduce scours in swine.

2. Technology Description

Acute indigestion resulting from the transition from a predominantly roughage diet to a feedlot diet could be fatal to ruminants. The purpose of a feedlot operation is to fatten a ruminant, such as beef cattle, for sale or slaughter. The most common and efficient method of fattening ruminants is to feed them a high grain or high energy concentrate diet. However, this abrupt conversion from a roughage or pasture diet of plant food, mainly cellulose, to a feedlot diet predominantly composed of grains and starches can cause decreased production to feedlot cattle and even death from acidosis. Similar diet transitions can result in a decrease in milk production for dairy cows as well as death.

As discussed in *Diseases of Feedlot Cattle*, Second Edition, Lea & Febiger, p 292–293 (1971), acute indigestion in cattle is caused by sudden consumption of large amounts of grain, green corn, green apples or other easily fermentable feeds. During a roughage diet, cellulosic bacteria predominates in ruminal microflora. Volatile fatty acids are usually formed in the following proportions: acetic, 67%; propionic, 19%; and butyric, 14%. These acids constitute an important nutrient from cellulose digestion. However, during the fattening process at the feedlot, cattle are placed on a high grain diet. On a high grain diet, the ruminal microflora ferment the new feed and produce 100 or more milli-moles per liter of lactic acid resulting in the rumen becoming immobilized. A large portion of the lactic acid accumulated may be the D(−) isomer which is an unavailable energy source for the ruminant and thus builds up in the rumen. Absorption of the acid into the blood lowers the blood pH and diminishes the content of bicarbonate and glucose bringing about acidosis. Compensation for the acidic condition occurs by excretion of carbonic acid through rapid respiration and by excretion of hydrogen ions through urine. Affected cattle may survive through compensation, however, severe acidosis is fatal. Additionally, the increase in acidity of the rumen damages the mucosa which may result in necrosis of the epithelium which enables bacteria such as *Spherophorus necrophorus* to enter the veins and be conveyed to the liver where liver abscesses may form in surviving animals.

Lactic acid and products containing lactic acid have been found to enhance gains in the starting period of cattle (first 28 days) and reduce liver abscesses when given prior to the transition from a roughage diet to a feedlot diet. Various strains of *Lactobacillus acidophilus* have been isolated which restore and stabilize the internal microbial balance of animals. Manfredi et al, U.S. Pat. No. 4,980,164, is such a strain of *Lactobacillus acidophilus* which has been isolated for enhancing feed conversion efficiency. The *Lactobacillus acidophilus* strain of the Manfredi et al patent has been designated strain BT1386 and received accession number ATCC No. 53545 from the American Type Culture Collection in Rockville, Md. Strain ATCC 53545 demonstrates a greater propensity to adhere to the epithelial cells of some animals which would increase the bacteria cultures' ability to survive, initiate and maintain a population within an animal intestine. Thus, the primary mode of action as previously understood relative to *Lactobacillus acidophilus* occurs post-ruminally.

Another strain of *Lactobacillus acidophilus* isolated for restoring and stabilizing the internal microbial balance of animals is disclosed in Herman et al, U.S. Pat. No. 5,256,425. The *Lactobacillus acidophilus* strain of the Herman et al patent has been designated strain BT1389 and received accession number ATCC No. 55221 from the American Type Culture Collection in Rockville, Md. Strain ATCC 55221 is a further improvement on strain ATCC 53545 in that it is easily identified and quantified due to its resistance to antibiotics such as erythromycin and streptomycin.

The above-mentioned strains of *Lactobacillus acidophilus* are perfectly good lactic acid producing organisms. However, more than a lactic acid producing organism is needed to improve the utilization of feedstuffs by ruminants, especially during the transition from a roughage diet to a feedlot diet. The problem with the increase of D-lactate in the rumen must also be resolved in order to facilitate the transition of ruminants from a roughage diet to a feedlot diet.

Administration of bacteria to cattle is also problem due to the extreme sensitivity of organisms like *Lactobacillus acidophilus* which are difficult to maintain in a viable state at ambient temperatures. Also, lactic acid is corrosive to feedlot and feedmill equipment and metallic components U.S. Pat. Nos. 5,534,271 and 5,529,793 suggest that both a lactic acid producing culture as well as a lactate utilizing bacterial culture be combined with a typical animal feedlot diet to assist in the transition of a ruminant diet from roughage to feedlot while minimizing the risk of acidosis. These patents list several classes of materials from each of the producing and utilizing categories which may be selected for combination with the animal feedstock. Unfortunately, these patents do not give much guidance as to which of these specific cultures should be selected in order to gain efficacious results. The only lactate utilizing cultures which are specifically enabled by the examples are *Propionibacterium* P-5, *Propionibacterium* P-42 and *Propionibacterium* P-99 and the only lactic acid producing cultures enabled by the examples are *Lactobacillus acidophilus* ATCC 53545 and *Lactobacillus acidophilus* strain LA45. The reference fails to disclose or suggest that amongst the thousands of permutations possible presented by their proposed combination of cultures, that synergistic results can occur by selecting a very specific strain of lactate utilizing culture not specifically enabled in these patents. The inventors of the instant invention have discovered such a specific lactate utilizing culture, namely *Propionibacterium* P-63.

Despite the above teachings, there still exists a need in the art for a direct fed microbial for ruminants having a specifically defined lactic acid utilizing culture which, when combined with lactic acid producing cultures, can demonstrate unexpected results in terms of efficacy against acidosis.

In addition, there exists a need in the art for a direct fed microbial which may reduce scours in swine and companion animals as the above technology has been more specifically directed against treatment of acidosis in ruminants.

BRIEF SUMMARY OF THE INVENTION

In accordance with the present invention a novel direct fed microbial for ruminants having a specifically defined lactic acid utilizing culture which, when used alone as a direct fed microbial or combined with lactic acid producing cultures, can demonstrate unexpected results in terms of resistance against acidosis is provided. More specifically, the lactic acid utilizing culture comprises *Propionibacterium* P-63. This increased resistance can enable the ruminant to be superior producers of milk, if dairy ruminants, or experience greater weight gain, if beef ruminants. This culture may also be used to reduce scours in swine.

A first embodiment of the present, invention comprises a ruminant direct fed microbial composition of matter comprising an acidosis inhibiting effective amount of *Propionibacterium* P-63. In most embodiments, the microbial composition is combined with an animal feed material selected from the group consisting of corn, dried grain, alfalfa, corn meal and mixtures thereof.

In the preferred embodiment, the direct fed microbial composition further comprises a lactic acid producing bacterial culture, and even more preferably *Lactobacillus acidophilus* ATCC 53545.

A second embodiment comprises a swine direct fed microbial composition of matter comprising a scour inhibiting effective amount of *Propionibacterium* P-63.

Still another embodiment of the present invention comprises a process for reducing acidosis when converting a ruminant diet from a roughage diet to a grain diet by administering to a ruminant a direct fed microbial comprising an acidosis inhibiting effective amount of *Propionibacterium* P-63.

In most embodiments, the microbial composition is combined with an animal feed material selected from the group consisting of corn, dried grain, alfalfa, corn meal and mixtures thereof.

Yet another embodiment comprises a process for reducing scours in swine by administering to a swine a direct fed microbial comprising an scour inhibiting effective amount of *Propionibacterium* P-63.

In a preferred embodiment, the direct fed microbial composition further comprises a lactic acid producing bacterial culture for administration to the ruminant, and even more preferably *Lactobacillus acidophilus* ATCC 53545.

An object of the present invention is to provide a novel direct fed microbial for ruminants or swine.

Still another object of the present invention is to provide a process for reducing acidosis in ruminants when converting from a roughage diet to a grain diet.

A further object of the present invention is to provide a synergistic combination of lactic acid producing cultures with lactate utilizing cultures to reduce acidosis in ruminants when converting from a roughage diet to a grain diet.

Another object of the present invention is directed to a method for reducing scours in swine.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

*Propionibacterium* P-63 is a culture of the species *propionibacterium jensenii*, strain designation PJ54. This information is obtained from Communicable Disease Laboratory, in Atlanta, Ga., U.S.A. Genetic equivalents of this strain are expressly considered to be covered within the scope of the present invention.

The use of lactate utilizing bacteria in ruminant feeds, even those feeds designed to aid in the conversion of the ruminant from a roughage diet to a grain diet is not considered novel. The prior art is replete with listings of many genus/species and strains of materials suggested for ruminant feeds. Prior to the present invention it is not believed that the use of *Propionibacterium* P-63 has been disclosed or suggested for use in animal feeds. The inventors have surprisingly discovered that this specific strain demonstrates superior anti-acidosis properties as compared to other lactate utilization bacteria. While not wishing to be bound to any specific scientific theory, use of this strain of bacteria during conversion of the ruminant feed from a roughage diet to a feedlot diet does not result in an appreciable production of lactic acid in the rumen, allowing it to remain at a relatively constant pH.

It is also believed that P-63 can be effectively used to treat scours in swine by administering a scour inhibiting amount of P-63 to a swine.

In practice, the amount of *Propionibacterium* P-63 which should be administered to the animal ranges between about $1 \times 10^6$ cfu/animal/day to about $1 \times 10^{12}$ cfu/animal/day. Higher amounts of the bacterium are preferably used, i.e., greater than about $1 \times 10^9$ cfu/animal/day when the bacterium is the sole acidosis or scours control agent whereas lesser amounts, i.e., less than about $1 \times 10^8$ cfu/animal/day may be administered when a lactic acid producing bacterium culture is added in combination with the P-63.

The bacterium culture may be administered to the ruminant in one of many ways. The culture can be administered in a solid form as a veterinary pharmaceutical, may be distributed in an excipient, preferably water, and directly fed to the animal, may be physically mixed with feed material in a dry form, or, in a most preferred embodiment, the culture may be formed into a solution and thereafter sprayed onto feed material. The method of administration of the culture to the animal is considered to be within the skill of the artisan.

When used in combination with a feed material, the feed material is preferably grain based. Included amongst such feed materials are corn, dried grain, alfalfa, and corn meal and mixtures thereof.

The bacteria cultures of the novel process may optionally be admixed with a dry formulation of additives including but not limited to growth substrates, enzymes, sugars, carbohydrates, extracts and growth promoting micro-ingredients. The sugars could include the following: lactose; maltose; dextrose; malto-dextrin; glucose; fructose; mannose; tagatose; sorbose; raffinose; and galactose. The sugars range from 50–95%, either individually or in combination. The extracts could include yeast or dried yeast fermentation solubles ranging from 5–50%. The growth substrates could include: trypticase, ranging from, 5–25%; sodium lactate, ranging from 5–30%; and, Tween 80, ranging from 1–5%. The carbohydrates could include mannitol, sorbitol, adonitol and arabitol. The carbohydrates range from 5–50% individually or in combination. The micro-ingredients could include the following: calcium carbonate, ranging from 0.5–5.0%; calcium chloride, ranging from 0.5–5.0%; dipotassium phosphate, ranging from 0.5–5.0%; calcium phosphate, ranging from 0.5–5.0%; manganese proteinate, ranging from 0.25–1.00%; and, manganese, ranging from 0.25–1.00%.

While the P-63 culture may be used alone in a method to prevent acidosis or scours, because of the high levels of administration required and the desire for even better resistance against disease, it is optionally combined with a lactic acid producing culture. Despite the above, it is hypothesized that one does not need a lactate producer in a beef direct fed microbial (DFM) to prevent/reduce acidosis. If the reason (or at least primary contributor) acidosis occurs is lactate production, adding a lactate producing organism with the DFM may likely be inconsequential. It is further hypothesized that a lactic acid producing culture may not be required when using P-63 to prevent scours in swine.

If added, the lactic acid producing bacteria could include, but is not limited to, the following: *Lactobacillus acidophilus; Lactobacillus plantarum; Streptococcuus faecium; Lactobacillus casei; Lactobacillus lactis; Lactobacillus enterii; Lactobacillus fermentum; Lactobacillus delbruckii; Lactobacillus helveticus; Lactobacillus curvatus; Lactobacillus brevis; Lactobacillus bulgaricus; Lactobacillus cellobiosuus; Streptococcus lactis; Streptococcus thermophilus; Streptococcus cremoris; Streptococcus diacetylactis; Streptococcus intermedius; Bifidobacterium animalis; Bifidobacterium adolescentis; Bifidobacterium bifidum; Bifidobacterium infantis; Bifidobacterium longum; Bifidobacterium thermephilum; Pediococcus acidilactici*; and, *Pediococcus pentosaceus*. Particularly preferred is the use of *Lactobacillus acidophilus*, and most preferably the strain corresponding to ATCC 53545.

When a lactic acid producing culture is utilized in combination with P-63, In practice, the amount of lactic acid producing culture which should be administered to the animal ranges between about $1 \times 10^6$ cfu/animal/day to about $1 \times 10^{12}$ cfu/animal/day, with amounts ranging from about $1 \times 10^7$ cfu/animal/day to about $1 \times 10^9$ cfu/animal/day being most preferred.

The invention is described in greater detail by the following non-limiting examples.

EXAMPLE 1

Bacterial Strains.

*Propionibacterium* cultures used in this study are obtained from the culture collection of Agtech Products, Inc., Waukesha, Wis. Cultures are maintained at −75° C. in a sodium lactate broth (NLB) supplemented with 10% glycerol (Hofherr and Glatz, 1983). The specific propionibacteria strains used in this study are listed in Table 1.

TABLE 1

*Propionibacterium* strains

| Strain number | Species designation | Strain designation | Source |
|---|---|---|---|
| P2 | P. acidipropionici | 128 | B |
| P3 | P. acidipropionici | E14 | A |
| P4 | P. thoenii | TH25 | A |
| P5 | P. acidipropionici | E214 | A |
| P9 | P. acidipropionici | 129 | B |
| P10 | P. thoenii | R9611 | A |
| P15 | P. thoenii | TH20 | A |
| P20 | P. thoenii | TH21 | A |
| P21 | P. thoenii | R6 | A |
| P25 | P. jensenii | J17 | A |
| P26 | P. thoenii | 8266 | B |
| P31 | P. freudenreichii | 1294 | E |
| P35 | P. acidipropionici | 1505 | E |
| P38 | P. acidipropionici | 13 | D |
| P41 | P. jensenii | 14 | D |
| P42 | P. acidipropionici | 10 | D |
| P44 | P. jensenii | 363 | E |
| P46 | P. jensenii | E.1.2 | F |
| P48 | P. freudenreichii | E.11.3 | F |
| P49 | P. freudenreichii | E.15.01 | F |
| P50 | P. acidipropionici | E.7.1 | F |
| P52 | P. acidipropionici | E.5.1 | F |
| P53 | P. acidipropionici | E.5.2 | F |
| P54 | P. jensenii | E.1.1 | F |
| P63 | P. jensenii | PJ54 | G |
| P68 | P. jensenii | PJ53 | G |
| P69 | P. jensenii | PJ23 | G |
| P74 | P. jensenii | PZ99 | G |
| P78 | P. acidipropionici | PA62 | G |
| P79 | P. thoenii | PT52 | G |
| P81 | P. acidipropionici | PP798 | G |
| P85 | P. thoenii | 20 | H |
| P86 | P. jensenii | 11 | H |
| P88 | P. jensenii | 22 | H |
| P89 | P. freudenreichii | 5571 | I |
| P90 | P. acidipropionici | 5578 | I |
| P96 | P. freudenreichii | 8903 | I |
| P99 | P. freudenreichii | ATCC 9615 | J |
| P101 | P. freudenreichii | ATCC 9617 | J |
| P104 | P. freudenreichii | ATCC 6207 | J |
| P105 | P. thoenii | ATCC 4871 | J |
| P106 | P. jensenii | ATCC 4964 | J |
| P108 | P. acidipropionici | ATCC 14072 | J |
| P111 | P. acidipropionici |  | O |

Sources: (A) Cornell University, Ithaca, NY; (B) Iowa State University, Ames IA; (C) Dr. K W Sahli, Station Federale D'Industrie Laitiere Liebefeld-Bern, Switzerland; (D) Dr. W. Kundrat, University of Munich, Munich, Germany; (E). Dr. V. B. D. Skerman, University of Queensland, Brisbane, Australia; (F) Dr. C. B. van Neil, Hopkins Marine Station, Pacific Grove, CA; (G) Communicable Disease Laboratory, Atlanta, GA, (H) Isolated from Gruyere cheese imported from France, (J) American Type Culture Collection, Rockville, MD; (O). Origin unknown.

Culture conditions. Strains are activated by placing a portion of the frozen suspension in 10 ml of NLB and incubating at 32° C. for 36–48 hours. Strains are subcultured by transferring a 1% volume of the culture at mid-log growth to fresh NLB. Cultures are transferred a minimum of three times before being tested. The purity of tested strains is monitored by regularly streaking cultures onto a sodium lactate agar (NLA).

In vitro acidified and neutralized broth medium. Primary strain selection involves testing the growth and lactic acid utilization of cultures in a basal broth media. The acidified medium is prepared by including 80 mM L(+) lactic acid in a basal broth containing 1% yeast extract, 1% tryptone, dipotassium phosphate and distilled water. The pH of the broth medium is raised to pH 5.0 using 5.0 M NaOH. Following filter sterilization (Gelman Sciences, Ann Arbor, Mich.), the medium is dispensed at a volume of 10 ml into sterile screw cap test tubes. Neutralized broth medium is prepared the same as acidified media except that the pH of broth is raised to 7.0 with 5.0 M NaOH prior to filter sterilization.

Rumen fluid simulation medium. Ruminal fluid is collected via ruminal cannula 2 h post feeding from a crossbred beef heifer fed a high roughage diet. The ruminal fluid is strained through four layers of cheesecloth and transported to the laboratory in an insulated container. Test ruminal fluid media contains 250 ml of strained ruminal fluid, 62.5 ml McDougall's buffer (McDougall, 1948), and 1.5% dextrose. The added dextrose serves as a readily fermented carbohydrate to simulate conditions found in the rumen of animals following grain engorgement. Strained ruminal fluid, buffer, and dextrose are dispensed into sterilized 500 ml bottles and allowed to equilibrate in a water bath at 39° C. for approximately 15 minutes prior to inoculation. Initial pH of the rumen fluid model ranged from 6.6 to 6.9 depending on date of collection.

High pressure liquid chromatography. Samples are prepared for HPLC analysis by aseptically removing 1.0 ml from the test medium at the appropriate sampling times. Samples are placed in a 1.5 ml microcentrifuge tube and the cells are pelleted by centrifugation (10 minutes, at 12,500 rpm). A sample of the supernatant fluid (0.5 ml) is transferred to a clean tube and acidified with an equal volume of 0.01 M sulfuric acid solution to stop fermentation. These samples are stored at −20° C. until analysis is performed. For analysis, frozen tubes are allowed to thaw at room temperature and filtered through 0.2 um filters directly into 2 ml HPLC autosampler vials and capped.

Samples are analyzed using a Hewlett Packard 1090 HPLC system equipped with a diode-array detector (Hewlett Packard, Atlanta, Ga.). The sample is injected into 0.005 M $H_2SO_4$ mobile phase heated to 65° C. and separated using a BioRad HPX-87H column (Bio-Rad Laboratories, Inc., Hercules, Calif.). The peaks are detected with a diode array detector at 210 nm. Other wavelengths are recorded and examined for peak purity, but 210 nm is the optimum setting for determining peak height with minimum background noise. Peak areas are used to determine compound concentrations by comparison with external standards. Peak purity is monitored by UV scanning techniques as an aid in identifying abnormal wavelength patterns present in a single peak.

Rumen model experimental procedures. Duplicate bottles are inoculated with the appropriate propionibacteria strain to be tested at a level of $1 \times 10^7$ cfu/ml. Bottles are flushed with $CO_2$, capped, and incubated at 39° C. for 48 h. Every 6 h during the 48 h incubation period, samples are collected and analyzed for pH, lactic acid and volatile fatty acid (VFA) concentrations. Additional samples are collected at 16 h and 48 h for use in microbiological analysis. Lactic acid and VFA samples are prepared by aseptically collecting a 1 ml sample in a 1.5 ml microcentrifuge tube. Cells are pelleted by centrifugation (10 minutes at 12,500× g). One-half ml of supernatant is mixed with an equal volume of 10 mM $H_2SO_4$ and filtered through a 0.2 um membrane filter.

Microbiological analysis consists of plating serial dilutions ($10^{-3}$, $10^{-4}$ and $10^{-5}$) of the in vitro rumen fluid medium on a propionibacteria selective-differential medium (PSA). Colonies with typical propionibacteria morphology are confirmed using pulsed-field gel electrophoresis (PFGE).

Differences in pH and lactic acid concentration between inoculated and uninoculated controls at each sampling time are calculated and regressed against incubation time up to 24 h in order to select the best lactic acid utilizing strains. Strains for which a change over time in lactate or pH was detected (an R>0.50 against sampling time) are compared using Duncan's Multiple Range procedures (SAS, 1985). Additionally, Gompertz equation is used to analyze the sigmoidal curves for pH decrease and lactic acid concentration increase (Zwietering et al. 1990).

Results. The rate of change in pH and lactic acid concentration is determined by regressing the difference between inoculated and control rumen fluid incubations against time. Only when the regression coefficient for rate of change in pH and lactate was greater than 0.50 for an inoculated flask was the data, included in the statistical analysis (Table 2).

TABLE 2

Impact of added *Propionibacterium* strains on rates of change in pH and lactate concentration of incubated rumen fluid models.

| Strain | pH elevation, (Units/h) | Lactate decrease (mM/h) |
|---|---|---|
| 42 | .03770 | 1.61 |
| 63 | .03627 | 1.30 |
| 54 | .02433 | 1.26 |
| 25 | .02380 | 1.12 |
| 41 | .02372 | 1.55 |
| 111 | .01691 | 1.05 |
| 81 | .01064 | .71 |
| 104 | .00923 | .88 |
| 89 | .00785 | .53 |
| 88 | .00590 | .76 |
| 49 | .00425 | .65 |
| 48 | .00366 | NA |
| 99 | .00051 | −.17 |
| 31 | .00026 | −.22 |
| 90 | −.00917 | −.32 |

Calculated by regressing the difference between inoculated and control fluid against incubation time.
Means in a column with the same superscript are not different (P < .05).

Compared with other strains, P42 has the highest rate of pH increase (0.0377 units/h), but is not statistically (P<0.05) different from strains P63, P54, P25, and P41. Strain P42 also has the highest rate of lactic acid utilization (1.61 mM/h) compared to others but is not statistically (p<0.05) different from strains P63, P54, P25, P41, P111, P81, and P104. Since linear regression analysis does not adjust for differences in lag times, other non-linear methods were employed Ruminal fluid simulation data is analyzed using the Gompertz non-linear equation technique. Values up to 24 h are used in the analysis since a decrease in lactic acid concentration is observed after 24 h in all controls. Flasks inoculated with strains P54 and P63 have significantly lower rates of hydrogen ion accumulation (Table 3).

TABLE 3

Contrasts of maximum lactate accumulation and minimum pH of rumen models inoculated with various propionibacteria strains.

| Strain | Lactate production rate (mM/h) | H+ increase rate (× 10$^{-5}$) | Time lag of lactate production (h) | Time lag of H+ increase (h) |
|---|---|---|---|---|
| P25 | 18.87 | 4.65 | 4.41+ | 4.20 |
| P31 | 38.85 | 11.63 | 5.15 | 3.81 |
| P41 | 23.31 | 11.15 | 4.65 | 3.29 |
| P42 | 24.42 | 7.46 | 5.52 | 3.99 |
| P48 | 38.85 | 1.45 | 5.45 | 3.27 |
| P49 | 6.67 | 6.45 | 5.89 | 3.28 |
| P54 | 21.09 | −1.45** | 8.08** | 3.56 |
| P63 | 9.99 | 2.18* | 6.47+ | 2.68 |
| P78 | 12.21 | 9.34 | 5.30 | 3.02 |
| P81 | 1.11 | 9.86 | 4.91 | 2.99 |
| P88 | 14.43 | 11.49 | 5.76 | 2.87 |
| P89 | 9.99 | 13.57 | 5.71 | 3.13 |
| P90 | 14.43 | 5.18 | 5.00 | 3.28 |
| P99 | 4.44 | 7.87 | 4.94 | 3.59 |
| P104 | −2.22 | 8.02 | 4.94 | 2.67 |
| P111 | 14.43 | 5.17 | 4.97 | 5.74* |
| Control | 38.85 | 17.99 | 5.45 | 4.72 |

*Values significantly different when compared to controls (P < 05)
+Values significantly different when compared to controls (P < .01)
**Values significantly different when compared to controls (P < .001)

When the rate of H$^+$ increase of inoculated flasks is compared to the control (0.00018), only strains P54 and P63 have significantly different values of −1.45 and 2.18 respectively. Strains P54, P63 and also P25 have a significant impact on the lactic acid production lag time. P54 and P63 increase the lag time of lactic acid accumulation by 2.06 and 2.63 (h) respectively, thereby slowing the accumulation of acid. On the other hand, strain P25 decreases the lag time of inoculated samples thus resulting in faster lactic acid accumulation. Strain P111 is the only strain found to significantly increase the lag time of H$^+$.

The viable plate counts of strains at 16 h and 48 h of incubation in the rumen simulation model are present in Table 4. Nine strains maintain a population of at least 1.0×10$^4$ cfu/ml for 48 hours. Six of the nine strains exceed 1.0×10$^5$ cfu/ml; strains P25 and P63 have the highest rates of survival at 6.0×10$^5$ and 1.0×10$^6$ cfu/ml, respectively.

TABLE 4

Survival of *Propionibacterium* strains in the rumen model after 16 and 48 hours of incubation.*

| | *Propionibacterium* (cfu/ml) | |
|---|---|---|
| Strain | 16 h | 48 h |
| 63 | 7.4 × 10$^6$ | 1.0 × 10$^6$ |
| 25 | 2.5 × 10$^5$ | 6.0 × 10$^5$ |
| 81 | 5.0 × 10$^6$ | 3.0 × 10$^5$ |
| 90 | 1.0 × 10$^4$ | 1.0 × 10$^5$ |
| 88 | 8.3 × 10$^6$ | 1.0 × 10$^5$ |
| 54 | 1.0 × 10$^5$ | 1.0 × 10$^5$ |
| 111 | 2.0 × 10$^6$ | 1.0 × 10$^4$ |
| 99 | 1.0 × 10$^4$ | 1.0 × 10$^4$ |
| 41 | 4.7 × 10$^6$ | 1.0 × 10$^4$ |
| 104 | 5.0 × 10$^6$ | 1.0 × 10$^3$ |
| 89 | 1.0 × 10$^3$ | 1.0 × 10$^3$ |
| 48 | 1.0 × 10$^5$ | 1.0 × 10$^3$ |
| 42 | 1.1 × 10$^6$ | 1.0 × 10$^3$ |
| 31 | 1.0 × 10$^3$ | 1.0 × 10$^3$ |

*Propionibacteria count at 0 hour was 1 × 10$^7$ cfu/ml

EXAMPLE 2

Seventy-five cross-bred, post weaned calves weighing 650–750 pounds are randomly assigned to one of three treatments: 1.) no treatment, 2.) *Propionibacterium* strain P63 treated at 3.0×10$^{11}$ cfu/hd, or 3.) *Propionibacterium* strain P63 at 1.0×10$^9$ cfu/hd and *Lactobacillus acidophilus* strain 53545 at 1.0×10$^8$ cfu/hd. A total of 15 pens with 5 calves per pen are blocked by sex, weight and breed prior to treatment assignment. Calves are given free access to the feed bunk and water source during the course of the experiment.

Each treatment group, consisting of steers and heifers are fed a 50:50 ration (cracked corn, cottonseed meal, alfalfa pellets and balanced for minerals) at 1.5 to 2% of BW for 14 days. During this period the appropriate treatment is added directly to the feed. The treatment dose for each individual pen is added to 600 ml of water and completely mixed with the daily ration at the time of feeding throughout the entire feeding study.

On the day following the 14-day establishment period, cattle do not receive any feed for a 24 h period. This procedure is performed in order to stimulate the engorgement of the next meal. Following the 24 hour fasting period, cattle are given a 90% concentration ration (75% cracked wheat and 25% cracked corn). This ration is fed for a total of 10 days. During this time, treatments are administered as stated above and cattle are closely monitored for signs of severe stress due to ruminal indigestion. Following the 10 day challenge period, cattle are fed a 90% concentrate diet consisting of 100% cracked corn. Cattle are fed to final weights of approximately 1,200 pounds (approx. 120 days).

All cattle are weighed at receiving and approximately every 28 days during the feeding period. Feed intake and animal health are monitored daily. Following the finishing period, cattle are transported to a packing plant at which time hot carcass weights, quality grades, yield grades, and carcass characteristics were determined.

Results. The only significant differences (p<05) in live weights are observed during the first 10 days of the study. Control cattle are 18 pounds heavier than cattle receiving the combination and 25 to 30 pounds heavier than cattle in the group which is fed P63 alone during this period. By day 27 no differences in live weight are observed (P<05). To reduce the variation resulting from bulk fill differences, final weights are determined using hot carcass weights and dressing percentages. Control carcass weights are 13 pounds heavier compared to cattle fed the combination and 18 pounds heavier than cattle fed P63 alone, however these differences are not statistically different and considered to be animal variation.

Feeding intake is reduced in cattle being fed the combination inoculum by 7.8% when compared to control animals during the first 83 days (p<0.02). Overall feed intake is 6.8% lower for the combination treatment (P<0.08) and only 2.8% lower when animals received P63 alone (not significant) when compared to controls.

The only significant difference in average daily gain is observed during the initial 10 days of the trial when cattle are abruptly switched from a 50% concentrate ration to a 90% concentrate diet containing 75% ground wheat. Cattle receiving the combination treatment gain 1.13 LB more than control cattle during this intensive adaptation period (p<0.04). Recall feed intakes during this period are not statistically different between treatment groups. Given the utilization of lactic acid and glucose by the combined inoculum the improvement in gain during this initial feeding period is expected since cattle are the most effected by ruminal indigestion at this time.

Average daily gains are slightly higher for cattle fed the combination during the first and last 30 days of the study. However, these differences are not significant. Cattle receiving P63 alone have slightly lower gains compared to control and cattle fed the combination inoculum during the entire study. Overall average daily gain (ADG) is almost identical during the 120 day feeding period.

Cattle which is fed the combination inoculum has significantly improved feed efficiencies over the entire 120 day feeding study when compared to controls. During the first 10 days of feeding, efficiency is improved by 38.4% (P<0.06) and by 10.4% (P<03) in the first 30 days when comparing cattle fed the combination to control cattle. The percent difference between treatments declines in the later periods of the feeding trial, however the significant treatment response of the combination inoculum during the initial period results in a significant treatment difference over the entire 120 day study (P<0.04).

No significant differences in carcass quality and composition are observed. The incidence of liver abscesses is relatively insignificant as compared to industry standards. Control and cattle fed P63 both have incidences of 8%. Cattle fed *Lactobacillus acidophilus* strain 53545 with *Propionibacterium* strain P63 have no liver abscesses. Generally, feedlot finished cattle will have a liver incidence of approximately 30%. Dressing percents, ribeye area, yield grades, and quality grades are similar for all treatments.

Having described the invention in detail and by reference to the preferred embodiments thereof, it will be apparent that modifications and variations are possible without departing from the scope of the appended claims.

What is claimed is:

1. A ruminant direct fed microbial composition of matter comprising:
    an acidosis inhibiting effective amount of *Propionibacteriuin* P-63; and
    an animal feed material wherein said animal feed material is selected from the group consisting of corn, dried grain, alfalfa, and corn meal and mixtures thereof.

2. The composition according to claim 1 further comprising additives selected from the group consisting of growth substrates, enzymes, sugars, carbohydrates, extracts and growth promoting micro-ingredients and mixtures thereof.

3. The composition according to claim 1 further comprising a lactic acid producing culture.

4. The composition according to claim 3 wherein said lactic acid producing culture is selected from the group consisting of *Lactobacillus acidophilus; Lactobacillus plantarum; Streptococcus faecium; Lactobacillus case; Lactobacillus lactis; Lactobacillus enterii; Lactobacillus fermentum; Lactobacillus delbruckii; Lactobacillus helveticus; Lactobacillus curvalus; Lactobacillus brevis; Lactobacillus bulgaricus; Lactobacillus cellobiosuus; Streptococcus lactis; Streptococcus thermophilus; Streptococcus cremoris; Streptococcus diacetylactis; Streptococcus intermedius; Bifidobacterium animalis; Bifidobacterium adolescenris; Bifidobacterium bifidum; Bifidobacterium infantis; Bifidobacterium longum; Bifidobacterium thermephilum; Pediococcus acidilactici;* and *Pediococcus pentosaceus* and mixtures thereof.

5. A ruminant direct fed microbial composition of matter comprising:
    an acidosis inhibiting effective amount of *Propionibacterium* P-63; and
    a lactic acid producing culture wherein said lactic acid producing culture comprises *Lactobacillus acidophilus* ATCC 53545.

6. A swine direct fed microbial composition of matter comprising:
    a scours inhibiting effective amount of *Propionibacterium* P-63; and
    an animal feed material wherein said animal feed material is selected from the group consisting of corn, dried grain, alfalfa, and corn meal and mixtures thereof.

7. The composition according to claim 6 further comprising additives selected from the group consisting of growth substrates, enzymes, sugars, carbohydrates, extracts and growth promoting micro-ingredients and mixtures thereof.

8. The composition according to claim 6 further comprising a lactic acid producing culture.

9. The composition according to claim 8 wherein said lactic acid producing culture is selected from the group consisting of *Lactobacillus acidophilus; Lactobacillus plantarum; Streptococcus faecium; Lactobacillus casei; Lactobacillus lactis; Lactobacillus enterii; Lactobacillus fermentum; Lactobacillus delbruckii; Lactobacillus helveticus; Lactobacillus curvatus; Lactobacillus brevis; Lactobacillus bulgaricus; Lactobacillus cellobiosuus; Streptococcus lactis; Streptococcus thermophilus; Streptococcus cremoris; Streptococcus diacetylactis; Streptococcus intermedius; Bifidobacterium animalis; Bifidobacterium adolescentis; Bifidobacterium bifidum; Bifidobacterium infantis; Bifidobacterium longum; Bifidobacterium thermephilum; Pediococcus acidilactici;* and *Pediococcus pentosaceus* and mixtures thereof.

10. A swine direct fed microbial composition of matter comprising:
    a scours inhibiting effective amount of *Propionibacterium* P-63; and
    a lactic acid producing culture wherein said lactic acid producing culture comprises *Lactobacillus acidophilus* ATCC 53545.

* * * * *